United States Patent [19]

Moots

[11] Patent Number: 5,576,476

[45] Date of Patent: Nov. 19, 1996

[54] SOYBEAN CULTIVAR A3732

[75] Inventor: Craig K. Moots, Taylorville, Ill.

[73] Assignee: Asgrow Seed Company, Kalamazoo, Mich.

[21] Appl. No.: 545,963

[22] Filed: Oct. 20, 1995

[51] Int. Cl.⁶ .............................. A01H 5/00; A01H 5/10; C12N 5/04

[52] U.S. Cl. .................. 800/200; 800/255; 800/DIG. 26; 435/240.48; 435/240.5; 47/58; 47/DIG. 1

[58] Field of Search ...................................... 800/200, 255, 800/DIG. 26; 435/240.48, 240.5; 47/58.03, DIG. 1

[56] References Cited

PUBLICATIONS

McBlain et al 1990, Regis. Flyer Soybean, Crop Sci 30:425.
McBlain et al 1990, Regis. Resnik soybean, Crop Sci 30:424–425.
Bahrenfus et al 1980, Regis. Pella Soybean, Crop Sci 20:415.
Fehr et al 1987, Regis. Pella 86 soybean, Crop Sci. 27:1313.
McBlain et al 1991. Regis. Edison soybean, Crop Sci 31:488–489.
Evaluation Maturity Groups III and IV; USDA Soybean Collection, 1969, pp. 7a–7d, 12a–12d.
McBlain et al 1990, Regis. GR8836 soybean, Crop Sci 30:425–426.
Grin Database Entry PI 437444, (9 Aug. 1994).
Grin Database Entry PI 548652, Bass soybean (9 Aug. 1994).
Grin Database Entry PI 547848, L79–908 soybean (9 Aug. 1994).
Grin Database Entry PI 547852, L80–5372 soybean (9 Aug. 1994).
Grin Database Entry PI 547827, L81–4274 soybean (9 Aug. 1994).
Plant Variety Protection Certificate for Soybean A3242.

*Primary Examiner*—Patricia R. Moody
*Attorney, Agent, or Firm*—Rothwell, Figg, Ernst & Kurz

[57] ABSTRACT

A novel soybean cultivar, designated A3732, is disclosed. The invention relates to the seeds of soybean cultivar A3732, to the plants of soybean A3732 and to methods for producing a soybean plant produced by crossing the cultivar A3732 with itself or another soybean variety. The invention further relates to hybrid soybean seeds and plants produced by crossing the cultivar A3732 with another soybean cultivar.

9 Claims, No Drawings

SOYBEAN CULTIVAR A3732

BACKGROUND OF THE INVENTION

The present invention relates to a new and distinctive soybean cultivar, designated A3732. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons lo to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior soybean cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same soybean traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new soybean cultivars.

The development of new soybean cultivars requires the development and selection of soybean varieties, the crossing of these varieties and selection of superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines as well as the phenotype of the hybrid influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Soybean, *Glycine max* (L), is an important and valuable field crop. Thus, a continuing goal of plant breeders is to develop stable, high yielding soybean cultivars that are agronomically sound. The reasons for this goal are obviously to maximize the amount of grain produced on the land used and to supply food for both animals and humans. To accomplish this goal, the soybean breeder must select and develop soybean plants that have the traits that result in superior cultivars.

SUMMARY OF THE INVENTION

According to the invention, there is provided a novel soybean cultivar, designated A3732. This invention thus relates to the seeds of soybean cultivar A3732, to the plants of soybean A3732 and to methods for producing a soybean plant produced by crossing the soybean A3732 with itself or another soybean line.

DEFINITIONS

In the description and tables which follow, a number of terms are used. In order to provide a clear and consistent understanding of the specification and claims, including the scope to be given such terms, the following definitions are provided:

Maturity Date. Plants are considered mature when 95% of the pods have reached their mature color.

Seed Yield (Bushels/Acre). The yield in bushels/acre is the actual yield of the grain at harvest.

Lodging Resistance. Lodging is rated on a scale of 1 to 5. A score of 1 indicates erect plants. A score of 2.5 indicates plants are leaning at a 45° angle in relation to the ground and a score of 5 indicates plants are laying on the ground.

Phytophthora Tolerance. Tolerance to Phytophthora root rot is rated on a scale of 1 to 5, with a score of 1 being the best or highest tolerance ranging down to a score of 5 which indicates the plants have no tolerance to Phytophthora.

Emergence. This score indicates the ability of the seed to emerge when planted 3" deep in sand and with a controlled temperature of 25° C. The number of plants that emerge each day are counted. Based on this data, each genotype is given a 1 to 5 score based on its rate of emergence and percent of emergence. A score of 1 indicates an excellent rate and percent of emergence, an intermediate score of 2.5 indicates average ratings and a 5 score indicates a very poor rate and percent of emergence.

Iron-Deficiency Chlorosis. Plants are scored 1 to 5 based on visual observations. A score of 1 means no stunting of the plants or yellowing of the leaves and a score of 5 indicates the plants are dead or dying caused by iron-deficiency chlorosis, a score of 2.5 means plants have intermediate health with some leaf yellowing.

Brown Stem Rot. This is a visual disease score from 1 to 5 comparing all genotypes in a given test. The score is based on leaf symptoms of yellowing and necrosis caused by brown stem rot. A score of 1 indicates no symptoms. Visual scores range to a score of 5 which indicates severe symptoms of leaf yellowing and necrosis.

Shattering. The amount of pod dehiscence prior to harvest. Pod dehiscence involves seeds falling from the pods to the soil. This is a visual score from 1 to 5 comparing all genotypes within a given test. A score of 1 means pods have not opened and no seeds have fallen out. A score of 2.5 indicates approximately 50% of the pods have opened, with seeds falling to the ground and a score of 5 indicates 100% of the pods are opened.

Plant Height. Plant height is taken from the top of soil to top node of the plant and is measured in inches.

DETAILED DESCRIPTION OF THE INVENTION

Soybean cultivar A3732 has superior characteristics and was developed from the cross A3242×Flyer. $F_2$ and $F_3$ plants were advanced by a modified pedigree selection. In 1990, $F_4$ progeny rows were grown in Illinois and selected based on agronomic characteristics. The highest yielding lines were retained for additional testing at two locations in 1991. Further testing and selections were conducted in 1992 at nine locations, at 20 locations in 1993 and at 25 locations in 1994. A3732 is a late maturity group III variety with resistance to races 3 and 14 of Soybean Cyst Nematode. It has no major gene for Phytophthora Root Rot. It is an improved plant type, with better lodging resistance and is adapted across all row widths and soil types.

A3732 has excellent yield potential and is adapted across the mid Group III growing area, especially where Soybean Cyst Nematode is present. This includes northeast Kansas, central Missouri, central and southern Illinois as well as central and southern Indiana.

Some of the criteria used to select in various generations include: seed yield, lodging resistance, emergence, disease tolerance, maturity, late season plant intactness, plant height and shattering resistance.

The cultivar has shown uniformity and stability for all traits, as described in the following variety description information. It has been self-pollinated a sufficient number of generations, with careful attention to uniformity of plant type to ensure homozygosity and phenotypic stability. The line has been increased with continued observation for uniformity. No variant traits have been observed or are expected in A3732.

Soybean cultivar A3732 has the following morphologic and other characteristics (based primarily on data collected at Stonington, Ill.):

This invention is also directed to methods for producing a soybean plant by crossing a first parent soybean plant with a second parent soybean plant, wherein the first or second soybean plant is the soybean plant from the line A3732. Further, both first and second parent soybean plants may be from the cultivar A3732. Therefore, any methods using the cultivar A3732 are part of this invention: selfing, backcrosses, hybrid breeding, and crosses to populations. Any plants produced using cultivar A3732 as a parent are within the scope of this invention. As used herein, the term "plant" includes plant cells, plant protoplasts, plant cells of tissue culture from which soybean plants can be regenerated, plant calli, plant clumps, and plant cells that are intact in plants or parts of plants, such as pollen, flowers, seeds, pods, leaves, stems, and the like. Thus, another aspect of this invention is to provide for cells which upon growth and differentiation produce the cultivar A3732.

The cultivar A3732 is similar to A3242. While similar, there are numerous differences. A3732 has tawny pubescence while A3242 has gray pubescence. A3732 has black hilum color and A3242 has imperfect black hilum color. A3732 is four days later in maturity than A3242.

TABLES

In the tables that follows, the traits and characteristics of soybean cultivar A3732 are compared to several competing varieties of commercial soybeans of similar maturity. In these tables, column 1 shows the Competitor Variety. Column 2 and 3 indicate the number of tests and years of testing. Column 4, 5 and 6 indicate the yield in bushels/acre for the instant invention, the Competitor Variety (in column 1) and the difference, respectively. Column 7 and 8 indicate the days of maturity for the instant invention and Competitor Variety, respectively and column 9 and 10 show the lodging score for the instant invention and the Competitor Variety respectively. Lodging scores are rated 1 =Best and 5 =Worst.

VARIETY DESCRIPTION INFORMATION

1. Seed Shape: Spherical Flattened (L/W ratio > 1.2; L/T ratio = < 1.2)
2. Seed Coat Color: (Mature Seed) - Yellow
3. Seed Coat Luster: (Mature Hand Shelled Seed) - Shiny
4. Seed Size: 14 grams per 100 seeds
5. Hilum Color: (Mature Seed) - Black
6. Cotyledon Color: (Mature Seed) - Yellow
7. Seed Protein Peroxidase Activity: High
8. Seed Protein Electrophoretic Band: Type B (SP1$^{b)}$)
9. Hypocotyl Color: Light purple below cotyledons
10. Leaflet Shape: Ovate
11. Leaflet Size: Medium
12. Leaf Color: Medium Green
13. Flower Color: Purple
14. Pod Color: Tan
15. Plant Pubescence Color: Brown
16. Plant Types: Intermediate
17. Plant Habit: Indeterminate
18. Maturity Group: III
19. Disease Reaction: Phytophthora Rot: Race 1 - Susceptible
    Race 3 - Susceptible
    Race 4 - Susceptible
    Soybean Cyst Nematode (*Heterodera glycines*)
    Race 1 - Susceptible
    Race 3 - Resistant
    Race 14 - Susceptible
20. Physiological Responses: Iron Chlorosis on Calcareous Soil: Susceptible
21. Plant Lodging Score: 1.8
22. Plant Height: 101 cm.
23. Seed Content - % Protein: 40.7
    % Oil: 19.2

TABLE 1

ASGROW RESEARCH TRIAL - HEAD TO HEAD COMPARISON
ASGROW A3732 vs. LISTED COMPETITORS
1992, 1993, 1994
ALL LOCATIONS

| Competitor Variety (Other) | Number | | Yield, Bushel/Acre | | | Maturity | | Lodging | |
|---|---|---|---|---|---|---|---|---|---|
| | Tests | Years | A3732 | Other | Diff. | A3732 | Other | A3732 | Other |
| Asgrow A3134 | 25 | 1 | 66.6 | 63.2 | 3.4 | 22.1 | 16.5 | 1.7 | 1.7 |
| Asgrow A3313 | 16 | 1 | 73.5 | 71.6 | 1.9 | 22.5 | 18.2 | 2.0 | 1.6 |
| Asgrow A3322 | 27 | 2 | 63.6 | 59.6 | 4.0 | 26.2 | 22.1 | 2.0 | 1.7 |
| Asgrow A3431 | 52 | 3 | 65.0 | 64.5 | .5 | 24.0 | 21.2 | 1.9 | 1.4 |
| Asgrow A3510 | 52 | 3 | 65.0 | 63.7 | 1.3 | 24.0 | 22.1 | 1.9 | 1.6 |
| Asgrow A3733 | 39 | 2 | 64.4 | 60.0 | 4.4 | 23.4 | 24.6 | 1.7 | 1.4 |
| Asgrow A3834 | 39 | 2 | 64.4 | 67.2 | −2.9 | 23.5 | 25.5 | 1.8 | 1.5 |
| Asgrow A3935 | 41 | 2 | 64.5 | 62.5 | 2.1 | 23.4 | 25.3 | 1.8 | 2.0 |
| Asgrow A4045 | 39 | 2 | 64.4 | 62.8 | 1.6 | 23.5 | 25.8 | 1.8 | 2.2 |
| Asgrow CI3948 | 30 | 2 | 65.8 | 66.9 | −1.1 | 23.3 | 26.3 | 1.8 | 1.6 |
| Depf CX394 | 21 | 1 | 66.3 | 60.0 | 6.2 | 21.5 | 22.2 | 1.7 | 1.6 |
| Pioneer 9392 | 37 | 2 | 64.6 | 63.2 | 1.4 | 23.8 | 22.6 | 1.7 | 1.6 |

TABLE 2

ASGROW RESEARCH TRIAL - HEAD TO HEAD COMPARISON
ASGROW A3732 vs. LISTED COMPETITORS
1994
ALL LOCATIONS

| Competitor Variety (Other) | Number | | Yield, Bushel/Acre | | | Maturity | | Lodging | |
|---|---|---|---|---|---|---|---|---|---|
| | Tests | Years | A3732 | Other | Diff. | A3732 | Other | A3732 | Other |
| Asgrow A3134 | 25 | 1 | 66.6 | 63.2 | 3.4 | 22.1 | 16.5 | 1.7 | 1.7 |
| Asgrow A3313 | 16 | 1 | 73.5 | 71.6 | 1.9 | 22.5 | 18.2 | 2.0 | 1.6 |
| Asgrow A3431 | 25 | 1 | 66.3 | 65.6 | .7 | 22.2 | 18.9 | 1.7 | 1.4 |
| Asgrow A3510 | 25 | 1 | 66.3 | 64.3 | 2.0 | 22.2 | 19.5 | 1.7 | 1.5 |
| Asgrow A3733 | 21 | 1 | 66.3 | 61.3 | 5.0 | 21.4 | 21.6 | 1.7 | 1.3 |
| Asgrow A3834 | 21 | 1 | 66.3 | 69.1 | −2.8 | 21.5 | 23.2 | 1.7 | 1.3 |
| Asgrow A3935 | 23 | 1 | 66.2 | 63.8 | 2.4 | 21.9 | 23.1 | 1.7 | 2.0 |
| Asgrow A4045 | 21 | 1 | 66.3 | 63.5 | 2.7 | 21.5 | 23.5 | 1.7 | 2.3 |
| Asgrow CI3948 | 21 | 1 | 66.3 | 67.0 | −.7 | 21.4 | 23.6 | 1.7 | 1.5 |
| Depf CX394 | 21 | 1 | 66.3 | 60.0 | 6.2 | 21.5 | 22.2 | 1.7 | 1.6 |
| Pioneer 9392 | 21 | 1 | 66.3 | 64.7 | 1.6 | 21.5 | 19.3 | 1.7 | 1.5 |

TABLE 3

ASGROW RESEARCH TRIAL - HEAD TO HEAD COMPARISON
ASGROW A3732 vs. LISTED COMPETITORS
1993
ALL LOCATIONS

| Competitor Variety (Other) | Number | | Yield, Bushel/Acre | | | Maturity | | Lodging | |
|---|---|---|---|---|---|---|---|---|---|
| | Tests | Years | A3732 | Other | Diff. | A3732 | Other | A3732 | Other |
| Asgrow A3322 | 18 | 1 | 62.1 | 58.9 | 3.2 | 26.2 | 22.4 | 1.8 | 1.6 |
| Asgrow A3431 | 18 | 1 | 62.4 | 62.5 | −.1 | 25.9 | 23.2 | 1.9 | 1.4 |
| Asgrow A3510 | 18 | 1 | 62.4 | 61.5 | .9 | 25.9 | 25.8 | 1.9 | 1.7 |
| Asgrow A3733 | 18 | 1 | 62.1 | 65.1 | 3.7 | 26.2 | 28.9 | 1.8 | 1.6 |
| Asgrow A3834 | 18 | 1 | 62.1 | 65.1 | −3.0 | 26.2 | 28.9 | 1.8 | 1.7 |
| Asgrow A3935 | 18 | 1 | 62.4 | 60.8 | 1.6 | 25.9 | 28.8 | 1.9 | 1.9 |
| Asgrow A4045 | 18 | 1 | 62.1 | 61.9 | .2 | 26.2 | 29.1 | 1.8 | 2.2 |
| Asgrow CI3948 | 9 | 1 | 64.7 | 66.7 | −2.0 | 27.6 | 32.7 | 2.1 | 1.6 |
| Pioneer 9392 | 16 | 1 | 62.4 | 61.3 | 1.0 | 27.9 | 28.4 | 1.8 | 1.7 |

TABLE 4

ASGROW RESEARCH TRIAL - HEAD TO HEAD COMPARISON
ASGROW A3732 vs. LISTED COMPETITORS
1992
ALL LOCATIONS

| Competitor Variety (Other) | Number | | Yield, Bushel/Acre | | | Maturity | | Lodging | |
|---|---|---|---|---|---|---|---|---|---|
| | Tests | Years | A3732 | Other | Diff. | A3732 | Other | A3732 | Other |
| Asgrow A3322 | 9 | 1 | 66.7 | 61.1 | 5.6 | 26.2 | 21.5 | 2.3 | 1.8 |
| Asgrow A3431 | 9 | 1 | 66.7 | 65.7 | .9 | 26.2 | 24.5 | 2.3 | 1.7 |
| Asgrow A3510 | 9 | 1 | 66.7 | 66.6 | .0 | 26.2 | 23.3 | 2.3 | 1.7 |

DEPOSIT INFORMATION

A deposit of the Asgrow Seed Company proprietary soybean cultivar A3732 disclosed above and recited in the appended claims has been made with the American Type Culture Collection (ATCC), 12301 Parklawn Drive, Rockville, Md., 20852. The date of deposit was Jun. 26, 1996. The deposit of 2,500 seeds were taken from the same deposit maintained by Asgrow Seed Company since prior to the filing date of this application. All restrictions upon the deposit have been removed, and the deposit is intended to meet all of the requirements of 37 C.F.R. §1.801–1.809. The ATCC accession number is ATCC 97635. The deposit will be maintained in the depository for a period of 30 years, or 5 years after the last request, or for the effective life of the patent, whichever is longer, and will be replaced as necessary during that period.

What is claimed is:

1. A soybean seed designated A3732, deposited as ATCC Accession Number 97635.

2. A plant or plants of the soybean cultivar designated A3732 produced by growing the seed of claim 1.

3. Pollen of the plant of claim 2.

4. Ovule or ovules of the plant of claim 2.

5. A soybean plant with all of the physiological and morphological characteristics of the soybean plant of claim 2.

6. Tissue culture of the plant of claim 2.

7. A soybean plant regenerated from the tissue culture of claim 6 wherein the regenerated soybean plant has all of the physiological and morphological characteristics of a plant grown from a soybean seed designated A3732.

8. A method to produce a hybrid soybean seed comprising the steps of:

a) planting in pollinating proximity seeds of soybean cultivar A3732, wherein the seeds of soybean cultivar A3732 are deposited as ATCC Accession Number 97635, and another soybean cultivar;

b) cultivating soybean plants resulting from said seeds until said plants bear flowers;

c) emasculating the male flowers of the plants of either one or the other soybean cultivar;

d) inducing cross pollination to occur between said soybean cultivars; and, e) harvesting seeds produced on said emasculated plants of the cultivar line.

9. A first generation ($F_1$) hybrid soybean plant produced by growing said hybrid soybean seed of claim 8.

* * * * *